United States Patent [19]

Poirier et al.

[11] Patent Number: 4,886,502

[45] Date of Patent: Dec. 12, 1989

[54] PERITONEAL ACCESS CATHETER

[75] Inventors: Victor L. Poirier, Chelmsford; Kurt A. Dasse, Needham; Mark A. Bowen, Stow; Benedict D. T. Daly, Wellesley, all of Mass.

[73] Assignee: Thermedics, Inc., Woburn, Mass.

[21] Appl. No.: 939,748

[22] Filed: Dec. 9, 1986

[51] Int. Cl.⁴ ............................................. A61M 5/32
[52] U.S. Cl. ............................ 604/175; 128/DIG. 26
[58] Field of Search ................ 604/175; 128/DIG. 26

[56] References Cited

U.S. PATENT DOCUMENTS

| | | |
|---|---|---|
| Re. 29,343 | 10/1974 | Amplatz . |
| 3,520,298 | 8/1967 | Lange . |
| 3,633,585 | 1/1972 | McDonald . |
| 3,663,965 | 5/1972 | Lee, Jr. ................................ 604/175 |
| 3,699,956 | 10/1972 | Kitrilakis . |
| 3,821,957 | 7/1974 | Riely . |
| 4,004,298 | 1/1977 | Freed . |
| 4,184,497 | 1/1980 | Kolff . |
| 4,190,047 | 2/1980 | Jacobsen . |
| 4,239,041 | 12/1980 | Popovich . |
| 4,256,102 | 3/1981 | Monaco . |
| 4,266,999 | 5/1981 | Bair ..................................... 604/175 |
| 4,278,092 | 7/1981 | Borsanyi et al. . |
| 4,351,333 | 9/1982 | Lazarus et al. . |
| 4,368,737 | 1/1983 | Ash . |
| 4,392,855 | 7/1983 | Oreopoulos . |
| 4,400,169 | 8/1983 | Stephen . |
| 4,405,305 | 9/1983 | Stephen et al. . |
| 4,405,314 | 9/1983 | Cope . |
| 4,405,320 | 9/1983 | Carcaver . |
| 4,416,657 | 11/1983 | Berglund . |
| 4,417,888 | 11/1983 | Cosentino et al. . |
| 4,484,912 | 11/1984 | Raible . |
| 4,488,877 | 12/1984 | Klein et al. . |
| 4,490,137 | 12/1984 | Moukheibir . |
| 4,496,349 | 1/1985 | Cobentino . |
| 4,553,960 | 11/1985 | Lazarus et al. . |
| 4,557,724 | 12/1985 | Gregonis . |
| 4,559,033 | 12/1985 | Stephen . |
| 4,559,039 | 12/1985 | Ash . |
| 4,569,675 | 2/1986 | Prose et al. . |
| 4,579,120 | 4/1986 | MacGregor . |
| 4,581,020 | 4/1986 | Mittleman . |
| 4,596,563 | 6/1986 | Pande . |
| 4,626,246 | 12/1986 | Verkahe ..................... 128/DIG. 26 |
| 4,668,222 | 5/1987 | Poirier ........................ 128/DIG. 26 |
| 4,687,471 | 8/1987 | Twardowski ....................... 604/175 |
| 4,699,155 | 10/1987 | Villari ................................ 128/762 |

FOREIGN PATENT DOCUMENTS

| | | |
|---|---|---|
| 666090 | 7/1963 | Canada ............................... 604/284 |
| 0081724 | 11/1981 | Fed. Rep. of Germany . |
| 86/01729 | 3/1986 | PCT Int'l Appl. ................ 604/175 |
| 2056282 | 12/1979 | United Kingdom . |

Primary Examiner—William L. Freeh
Attorney, Agent, or Firm—Lorusso & Loud

[57] ABSTRACT

Disclosed is an improved peritoneal access system for providing repeated, long term access through the peritoneum, as for patients undergoing peritoneal dialysis. The system includes a catheter tube extending through an implantable percutaneous access device (PAD) formed of a cylindrical neck and a buttonlike annular skirt. A portion of the catheter tube external to the PAD has a bellows integrally formed therein permitting the tube to be bent and moved without restricting fluid flow or stressing the PAD. The internal portion of the catheter tube has a sharp right angle below the PAD to tunnel the tube in a subcutaneous plane to the peritoneal penetration site and a position-adjustable collar for anchoring/sealing the cathether tube near the upper surface of the peritoneum.

13 Claims, 5 Drawing Sheets

PERITONEAL ACCESS CATHETER

BACKGROUND OF THE INVENTION

This invention relates to devices for permitting access to the body through the skin, i.e., percutaneous devices, and more particularly to continuous ambulatory peritoneal access catheters.

Continuous peritoneal access catheters are permanently implanted in the skin of patients who require repeated access to the peritoneum. For example, such catheters are implanted in patients who undergo peritoneal dialysis.

A problem with prior art devices is that movement of the external non-implanted portion of the catheter could cause injury. For example, U.S. Pat. No. 4,278,092 to Borsanyi et al. discloses a peritoneal catheter which has a catheter tube that is removable. Any movement of the external portion of the tube will be transferred to the retaining ring as well as to the internal portion of the catheter. Some protection from accidental movement of such prior art devices can be provided by taping and padding the external tubing to the patient. However, intentional movement of the external tubing, as for attachment and removal of dialysis equipment, may still disrupt the implant site and/or injure the patient.

Another drawback of presently available peritoneal catheters is that the internal portion of the catheter runs in essentially a straight line in alignment with the external portion of the catheter. Because of this configuration there is a substantial risk of an exit site infection which could lead to peritonitis.

Another drawback of presently available peritoneal catheters is that many fail to incorporate porous surfaces into which the peritoneum and adjacent tissue can grow for anchoring and sealing. Some catheters have such an interface but only at a fixed distance from the exit site, thus different sized catheters are required for different abdominal wall thicknesses.

Another drawback of presently available peritoneal catheters is that practical devices for long-term skin penetration in humans have not been successful because the skin adjacent to the implanted device would not heal to form a tight barrier to infection. Instead, when a foreign device was implanted, epidermal cells would begin to migrate, each seeking to surround itself completely with other similar cells. The epidermal cells would thus grow alongside of the device in search of its sister cell. Deep sinus tracts would form and body fluids would be exuded at the interface between the device and adjacent tissue thereby forming a bed for infection. The peritoneal device, if not expelled spontaneously, would have to be surgically removed to allow the infection to be cured. For example, British Pat. No. 2,056,282 discloses an implant device which would cause the cells to migrate because there is no textured surface into which the cells can grow.

Figure 1:
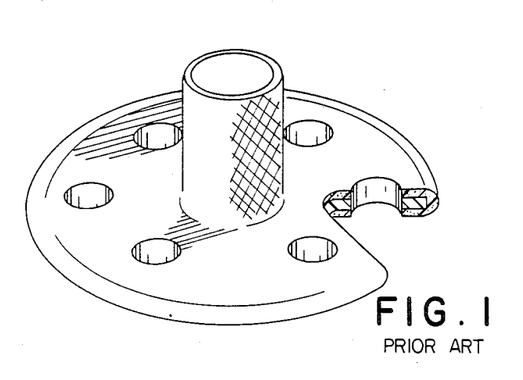
FIG. 1 is a perspective view of the known percutaneous access device described in U.S. patent application Ser. No. 613,931 labeled as PRIOR ART.

In copending U.S. Patent Application Ser. No. 613,931, entitled "Percutaneous Access Device" filed May 25, 1984 by Poirier et al., the teachings of which are incorporated herein by reference, some of the problems associated with prior art peritoneal access devices are obviated. As is shown in FIG. 1, the percutaneous access device (PAD) of this application, in its preferred form, resembles a button having a raised neck and a central hole or bore therethrough to accommodate a tube. The button includes a generally flat skirt and a neck substantially normal to the skirt. Both the skirt and neck are formed of a biocompatible material such as a semirigid polyurethane and are sized such that when the PAD is implanted its neck penetrates the epidermis and dermis and its skirt is anchored in the subcutaneous tissue. This PAD promotes formation of a tight barrier to infection by controlling the migration of epidermal cell downgrowth to provide a stable junction to ensure mechanical and biological stability.

One of the embodiments of the peritoneal access system or catheter of the present invention incorporates this type of PAD.

SUMMARY OF THE INVENTION

The invention is a peritoneal access system or catheter for long term skin penetration. The problems of the prior art peritoneal access catheters are reduced by a peritoneal access system in accordance with the present invention which, in one embodiment, includes a PAD of the type disclosed in U.S. Ser. No. 613,931 filed May 25, 1984, an external catheter tube with bellows to absorb shock and form a 90° corner so the external catheter can run parallel to the skins surface, an internal catheter tube with a sharp angle to tunnel the tube in a subcutaneous plane to the peritoneal penetration site, and an adjustable peritoneal collar to encourage rapid ingrowth of the peritoneum and/or adjacent tissue.

It is an object of the present invention to provide a peritoneal access system including a means for reducing the likelihood of injury to the patient when the external portion of the catheter is moved.

Another object of the present invention is to provide a peritoneal access system including a means to promote the incorporation of a skirt portion of the system into the integument.

Another object of the present invention is to provide a peritoneal access system which reduces the risk of infection.

Still another object of the present invention is to provide a peritoneal access system including a slidable collar to permit anchoring of the internal portion of the catheter and to accommodate abdominal walls of varying thicknesses, to enhance healing of the peritoneum, and to simplify surgical insertion of the device.

Yet another object of the invention is to provide a peritoneal access system in which the external portion of the catheter can make a sharp 90° bend before penetrating the skin.

DESCRIPTION OF PREFERRED EMBODIMENTS

In its broadest form, (see FIG. 2) the peritoneal access catheter system of the present invention is formed of two components: a catheter tube 79, and a percutaneous access device (PAD) 20.

Figure 2:
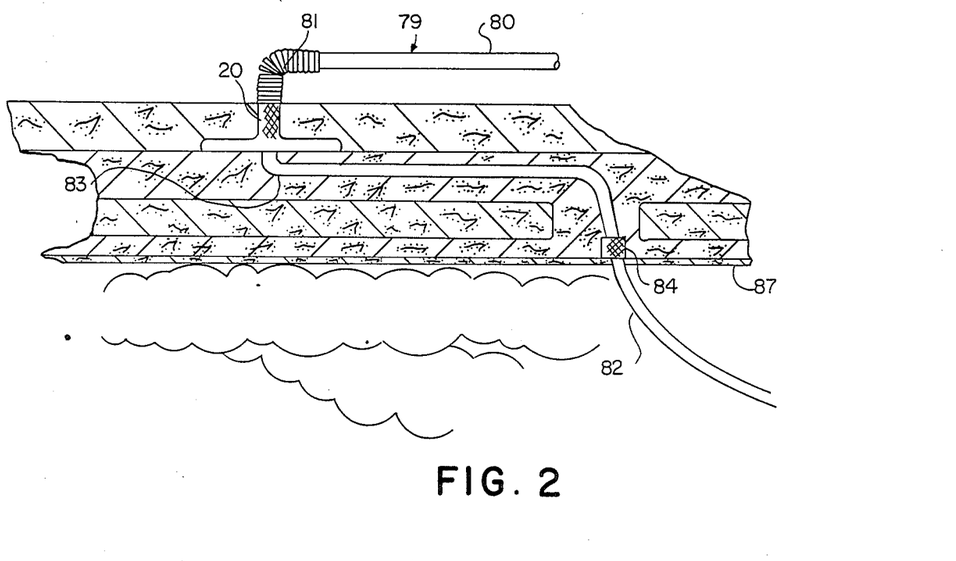
FIG. 2 is a cross sectional view of a peritoneal access catheter or system in accordance with the present invention, as implanted in a patient.

In a first embodiment, the catheter tube 79 is a long hollow tube formed of a nontoxic, biocompatible, semiflexible material such as a semirigid polyurethane. A suitable polyurethane is Tecoflex ® EG-80A material, a thermoplastic polyurethane available from Thermedics Inc. of Woburn, Mass., as set forth in U.S. Pat. No. 4,523,005 to Szycher entitled "Extrudable Polyurethane for Prosthetic Devices Prepared From a Diisocyanate, a Polytetramethylene Ether Polyol, and 1,4-Butane Diol." The catheter tube 79 is extruded as a hollow tube and then cut to length. The single catheter tube 79 can be thought of as including an external catheter tube 80 and an internal catheter tube 82.

The external catheter tube 80 includes an accordianly-pleated bellows section 81. The bellows section 81 acts like a shock absorber to help relieve any stress the PAD 20 or the internal catheter 82 might receive from movement of the external catheter 80. Prior to the present invention, the PAD 20, and thus the internal catheter 82, would be protected simply by taping and padding the external catheter to the patient. The present invention is advantageous in that it offers protection to the PAD 20 not only when the external tube is accidentally moved but even if the external catheter 80 is intentionally moved, for example, when the external dialysis equipment is attached or removed.

As is shown in FIG. 2, the bellows section 81 also allows the external catheter tube 80 to be at a ninety degree angle with respect to the neck of the PAD without restricting the flow of dialysate within the tube 80 and without exerting any pressure on the PAD 20. Such an orientation of the tube 80 makes it more convenient to tape the external catheter tube to the patient's body.

The bellows 81 is formed on the external portion 80 of catheter 79 after the catheter 79 has been cut to length. One method to form the bellows is by placing the catheter tube 79 in an appropriate female mold which is then heated to about 130° C. to soften the thermoplastic material. With one end of the catheter 79 sealed, a constant pressure of approximately 2.0 psi of nitrogen gas is applied to the other end for approximately 30 minutes to allow the tube to form in the shape of the mold. After the bellows 81 has been formed the catheter tube 79 is cooled down and removed from the mold.

The internal catheter tube 82 is perforated at its distal end to allow dialysate to easily exit the tube. One method of perforating the tube consists of punching small diameter holes through the wall of the catheter tube 82.

The portion of the catheter tube exiting from the base of the PAD 20 is fabricated with a sharp angle 83 of approximately 90 degrees. One method of accomplishing this sharp right angle 83 is by placing the tube on an appropriately-shaped mandrel and heat forming the tube. This angle allows the internal catheter tube to be tunnelled away from the skin penetration site in a infection that could lead to peritonitis.

Figure 6:
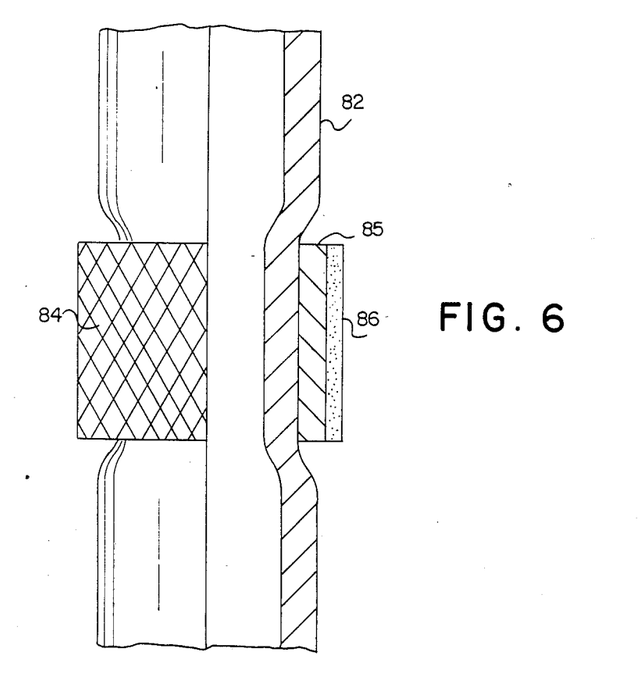
FIG. 6 is a cross-sectional view of the slidable peritoneal collar attached to the catheter.

The internal catheter tube 82 also incorporates an adjustable peritoneal collar 84 into which the peritoneum 87 and/or adjacent tissue can grow. The internal end of the peritoneal collar 84 is positioned in close approximation to the outer surface of the peritoneum to encourage rapid ingrowth and healing of the peritoneum, to prevent dialysate back leakage and to anchor the internal catheter. The peritoneal collar 84 is fabricated out of biocompatible materials such as the polyurethane mentioned above. As shown in FIG. 6, the sliding collar 84 is formed of a plastic polyurethane tube 85 covered with a porous polyurethane material 86. One method of producing the collar 84 is by winding, on a bias of approximately 45°, a polyurethane filament which is approximately 75 microns in diameter into multiple layers with the bias being reversed layer-to-layer, to achieve a porosity from filament to filament of approximately 75 to 400 microns. The porous structure 86 is diffusion bonded to tube 85 by heat treating at appropriate temperatures such as a temperature of about 110° C. A collar 84 is then cut to length and positioned by sliding it onto tube 82. The inside diameter of collar 84 is smaller than the outside diameter of tube 82 to form an interference fit between both members. This interference fit provides a stable seal as well as sufficient friction to prevent the collar from moving once it is properly positioned by the surgeon. The pores of the peritoneal collar 84 will encourage cellular ingrowth and attachment of the patient's peritoneal membrane and surrounding tissue to enhance wound healing at the access site.

The collar 84 which is configured to make a friction fit with the internal catheter 82 may be slid along the internal catheter tube 82 during implantation to adjust for differences in abdominal wall thickness. Once the proper position is found, the collar becomes fixed first by the friction fit and later by diffusion of the polyurethane between tubes 82 and 85. In addition, ingrowth of tissue into the porous structure 86 also provides stable anchoring of the collar 84.

The long-term percutaneous access device (PAD) shown and described herein overcomes the fundamental instability of known devices in that it promotes the formation of a tight, infection-free barrier at the skin surface. The biologic barrier or seal is the result of the use of the percutaneous access device 20 of the type set forth in U.S. Patent Application Ser. No. 613,931.

Figure 3:
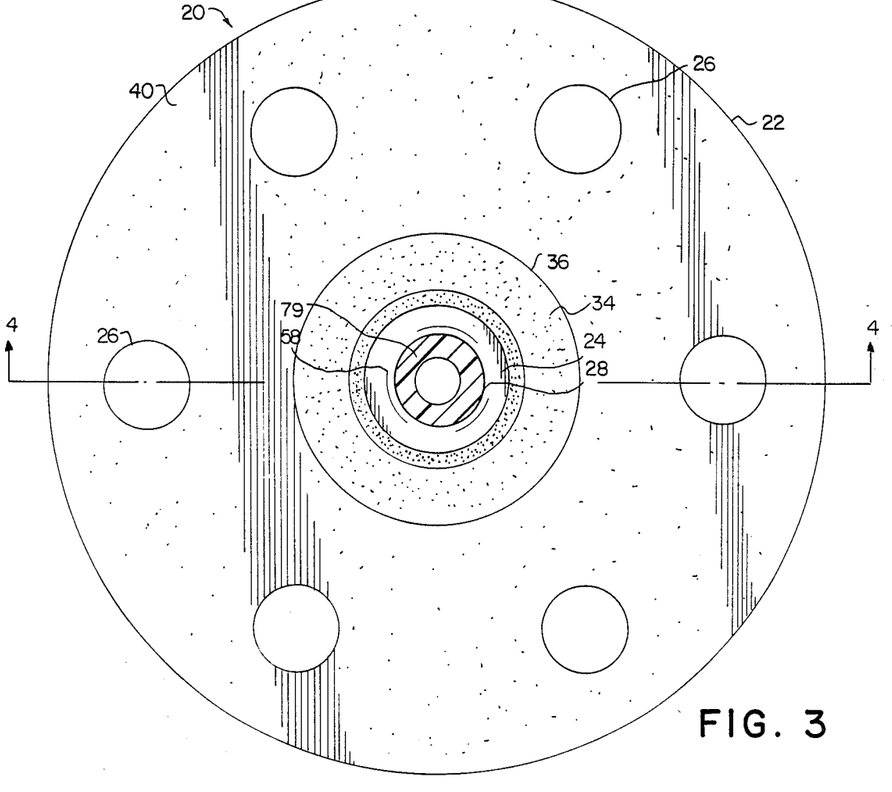
FIG. 3 is a top or plan view of the percutaneous access device (PAD) of FIG. 1 supporting a catheter in accordance with the present invention, with the catheter and portions of the PAD shown in section.
Figure 4:
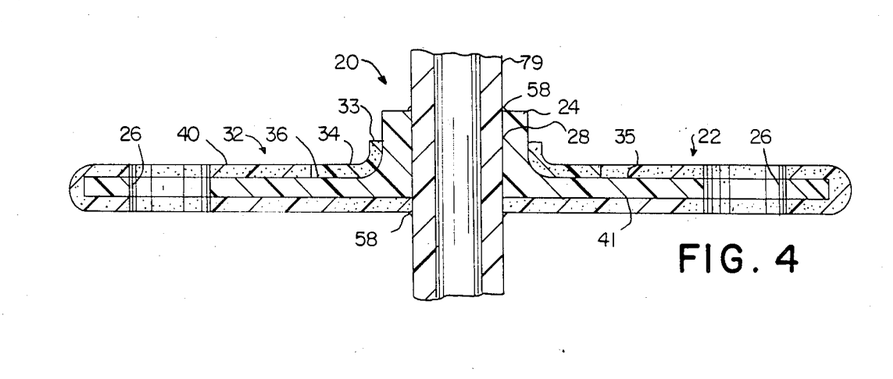
FIG. 4 is a cross-sectional view taken along the line 4—4 of FIG. 3.

Such a percutaneous device 20 for implantation in humans is best shown in FIGS. 1, 3 and 4. The PAD 20 is buttonlike in appearance and includes a generally flat flange or skirt 22 for anchoring the device and a hub or neck 24, preferably integral with and generally normal to the skirt 22. The skirt 22 and the neck 24 are formed of a nontoxic biocompatible semiflexible material such as a semirigid polyurethane. A suitable polyurethane is Tecoflex EG-60D, available from Thermedics Inc. of Woburn, Mass. Preferably the skirt 22 is disk-shaped and has a diameter in the range of about 0.8 to 1.8 inches and a thickness of about 0.010 to 0.100 inches. One or more holes 26 are provided in the skirt 22 to encourage tissue penetration for increased anchoring of the PAD 20 as well as encouraging lymphatic drainage. The neck 24 has a diameter of about 0.125 to 0.50 inches and flares upward from the skirt 22 a distance of about 0.08 to 0.40 inches so as to extend through the epidermal and dermal layers of a patient when the skirt 22 is implanted in the subcutaneous tissue (see FIG. 5). A central hole or bore 28 is provided in the neck 24 and also extends through the skirt 22 to accommodate the catheter 79 (FIG. 4).

Figure 5:
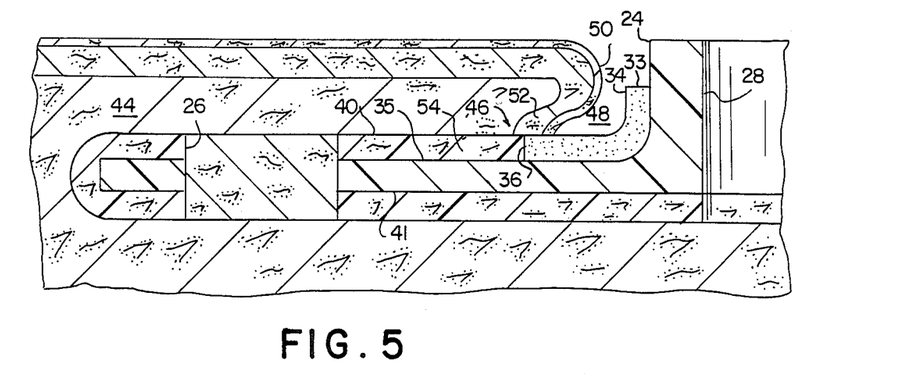
FIG. 5 is an enlarged cross-sectional view of one-half of the PAD of FIG. 4 illustrating in schematic form the histology associated with a stabilized, implanted PAD.

To promote healing of skin and the formation of a tight, infection-free barrier between the percutaneous access device 20 and adjacent tissues following implantation of the PAD 20, the skirt 22 and at least the lower potion of the neck 24 are covered by a two-stage porous bed 32. A first stage 34 of the bed 32 overlies the lower portion of the neck 24, preferably commencing at a location such that the top 33 of this first stage 34 is positioned at the epidermal layer when the PAD is implanted. The first stage 34 may also extend along part of the upper surface 35 of the skirt 22 — e.g., a distance of up to 0.25 inches, terminating at a junction 36 formed between adjacent ends of the first stage 34 and a second stage 40. The junction 36 between stage 33 and 40 can also be positioned at the corner between the neck 24 and the skirt 22.

A material for the first stage 34 of the porous bed can be 4 polytetrafluoroethylene (PTFE) having pore sizes of about 50–125 microns and a thickness of about 0.020 inches. For example, the first stage of the porous bed may be formed of Impra 15:1, a PTFE material available from Impra Inc., of Tempe, Arizona, and formed by extrusion followed by stretching to fifteen times the extruded length. The second stage 40 of the porous bed 32 covers at least the remainder of the upper surface 35 of the skirt 22 and preferably the lower surface 41 as well. This stage 40 of the porous bed 32 may be formed of a material such as a polyester velour (e.g. Dacron velour available as part No. 600K61121 from the United States Catheter and Instrument Company of Glenfalls, N.Y.) This material is a woven fabric with loose strands to allow for cell infiltration, and its pore sizes are considerably larger than those of the first stage 34 of the porous bed 32, typical values being about 100 to 800 microns.

Both porous stages are tightly bonded to the underlying substrate (the skirt 22 and the neck 24) by a suitable adhesive such as No. 1-MP polyurethane adhesive available from Thermedics Inc. of Woburn, Mass. To improve its biocompatibility, the Dacron velour may be chemically stripped, as by washing it in distilled water adjusted to a pH of 10.

It is essential to the successful long-term implantation of the percutaneous access device of the invention that the path length of the first stage 34 of the porous bed 32 along the neck 22 and the skirt 24, and the pore sizes of both stages 34 and 40, be properly selected to fulfill the different functions performed by these stages. Accordingly, the material of the first stage 34 has pores of about 75–400 microns in size, preferably about 75–125 microns, a size which permits downgrowth of epidermal cells, but at a rate far less than would occur in a material having larger pores. The biomaterial of the second stage has pores of about 75 to 800 microns in size, large enough to allow penetration and viability of cells such as fibroblasts which displace body fluids from these pores and synthesize collagen. The controlled rate of epidemal cell downgrowth allowed by the first stage length of about 0.25 inches, is sufficient to prevent epidermal cells from reaching the junction 36 between the stages 34 and 40 until mature collagen is formed in the pores of the second stage 40 (typically two to six months following implementation of the device 20).

The presence of mature collagen in the second stage 40 terminates the growth of epidermal cells at or near the junction 36, thus forming a stable, tight, dermal/biomaterial barrier.

For purposes of the invention described and claimed herein, pore size is defined as the diameter of a circle whose area is equal to the area of an equivalent opening or void in the bed structures. The pores may, for example, be formed between threads or filaments of the porous bed structures, the filaments preferably being utilized in multiple layers positioned to avoid alignment of pores in adjacent layers. The resulting structure of the porous bed stages has voids or pores which are interconnected along the length of the bed, permitting controlled growth of cells into the pores and strong mechanical bonding due to wrapping of cells and connective tissue around and in between the filaments. It is essential that the pores be interconnected so that collagen may be deposited and inhibit downgrowth of the epidermal cells.

The necessity of proper pore size selection and of a two-stage bed of porous material is indicated by the following discussion of the consequences of alternative structures. For example, were a single stage bed of small pore size material utilized in the percutaneous access device 20, such pores would not permit long-time survival of infiltrating fibroblasts and the formation of mature collagen needed to halt the growth of epidermal cells because of a lack of sufficient vascularization Were a single stage bed of large pore size material utilized, body fluids would be wicked to the external environment, providing a moist environment for bacterial infection. Note that even in a two stage bed, use in the first stage of material having pores which are too small will not sufficiently retard epidermal cell downgrowth since rapid downgrowth of epidermal cells will occur around the first stage. In each of the above-noted alternatives, no stable, infection-free barrier would form to permit long-term implantation of the percutaneous access device.

FIG. 5 shows in diagram form the skin and tissue structure adjacent to a stabilized implanted percutaneous access device 20 as disclosed herein. For ease of illustration, only one-half of the symmetrical PAD 20 is indicated and no tube is shown extending through the central bore 28. The histology illustrated, which is typical of that observed about six months after implantation of the device 20 in the subcutaneous layer 44, is characterized by a stable interface 46 between the skin and the PAD 20. The interface or barrier 46 is located near the junction 36 between the first stage 34 and the second stage 40 of the porous bed and lies at the end of a sinus 48 which forms and progresses downward and along the porous bed 32 during the 2–6 month period of stabilization of the implanted device 20. A thin epidermal layer 50 lines the sinus 48, and the connective tissue 52 in the interface 46 is similar to dermis. Mature collagen bundles 54 are present in the polyester velour second stage 40, and the implant site is generally infection-free. The interface 46 remains essentially stable for periods of one year or longer.

Percutaneous access devices having the general configuration shown in FIGS. 1–4 (but without a central bore 28 and tube) were implanted in various positions in pigs and many survived a full year before being electively explanted. Examination of the connective tissue of these devices showed structure similar to that of FIG. 5, including an interface near the junction of the two stages of the porous bed having mature dense collagen similar to dermis.

The first stage 34 of the porous bed may, instead of being formed of PTFE, be fabricated of multiple layers of filaments of a polyurethane such as Tecoflex EG-60D, available from Thermedics Inc. of Woburn, Mass. (Tecoflex is a registered trademark of Thermedics for medical grade urethane elastomeric materials). This polyurethane, which is formed as the reaction product of dicyclohexyl methane diisocyanate, polytetramethylene ether glycol, and 1,4 butane diol, has shown excellent cell attachment characteristics and biocompatibility in in vitro tests of several biomaterials with human skin fibroblasts. When used in the first stage of the porous bed, the filaments preferably have a diameter of from about 0.004 to 0.015 inches and are formed into a structure having about three to ten layers. The structure is fabricated such that it has spaces or open areas between filaments of about 0.001 to 0.004 inches (as measured from electron micrographs of surfaces and cross-sections of the porous bed). One method of fabricating the first stage 34 of the polyurethane filaments is to do so on a mandrel and then to form a bonded structure by heating the mandrel — for example, to a temperature of about 110 degrees Celsius for approximately one half hour. An alternative to heating the wound filaments is to overcoat them with an adhesive such as a dilute solution of the polyurethane Tecoflex EG-60D plus a solvent.

Tecoflex EG-60D polyurethane may also be used in the second stage of the porous bed in place of Dacron velour. A suitable loose mesh structure includes about 3 to 10 layers of filaments of 0.004 to 0.015 inch diameter formed with interfilament spacings of about 0.001 to 0.015 inches.

The first embodiment of the percutaneous access device 20 is assembled prior to implant with the catheter 79. To assemble the catheter system, the catheter tube 79 is stretched so that the angle 83 (FIG. 1) is substantially straight. The distal end of the catheter tube 79, less the peritoneal collar 84, is then fed through the central bore 28 of the percutaneous access device 20 until the bellows section 81 of the catheter tube contacts the PAD 20. The peritoneal collar may then slide onto the distal end of the internal portion of the catheter 82. A permanent seal or bond 58 of the PAD 20 to the catheter tube can be accomplished by using an adhesive such as 1-MP polyurethane adhesive available from Thermedics, Inc. of Woburn, Mass. Prior to implantation of the catheter system the peritoneal collar 84 is adjusted to fit the patient's peritoneum.

Figure 7:
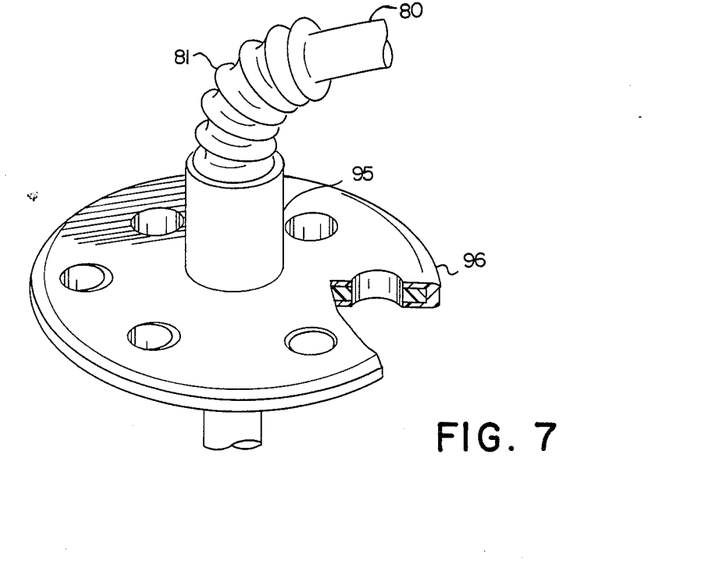
FIG. 7 is a perspective view of an alternate embodiment of a peritoneal access catheter in accordance with the present invention.

In a second embodiment of the peritoneal access catheter system, the percutaneous access device (PAD) is comprised of two separate pieces: a skirt 96 and a neck 95 (See FIG. 7).

In fabricating the percutaneous neck 95, an extruded Tecoflex EG-60D polyurethane tube is positioned on a mandrel and wrapped with 75 micron diameter filament composed of polyurethane obtained from Thermedics, Inc. Multiple layers are formed with a pore size of 50 to 200 microns. The tube is then heat treated at 110° C. for 30 minutes to fuse the strands to the tube and to themselves. The tube is then cut to lengths of 0.25 inches. At this point, the section of tube can be used as a peritoneal collar 84. If the section of tube is to be used as a percutaneous neck 95 one end is fused by pressing the end to a heated fixture thus melting filaments together as well as to the substrate tube.

The skirt 96 is fabricated by winding 75 micron filaments on a mandrel that is 1.0 inch in diameter. Multiple layers are produced with a pore size of 75 to 800 microns. The mandrel with the filament structure is then heated to 110° C. for 30 minutes to fuse the filaments together. The resulting tube is then removed from the mandrel and sectioned axially. The porous structure is then opened up and laid flat.

A 1.0 inch wide polyurethane tape approximately 0.010 to 0.020 thick is then extruded. The polyurethane tape can be made from Tecoflex EG-60D available from Thermedics, Inc. The flat porous structure is then placed on both sides of the extruded tape and heat treated between plates at 110° C. for 30 minutes to fuse the porous structure to the tape. Disks with a diameter of about 0.9 inches are then punched from the tape. Each disk then has six holes of approximately 0.08 inches in diameter drilled in it to provide for lymphatic drainage.

The catheter tube 79 is fabricated in the same manner as in the first embodiment.

Figure 8:
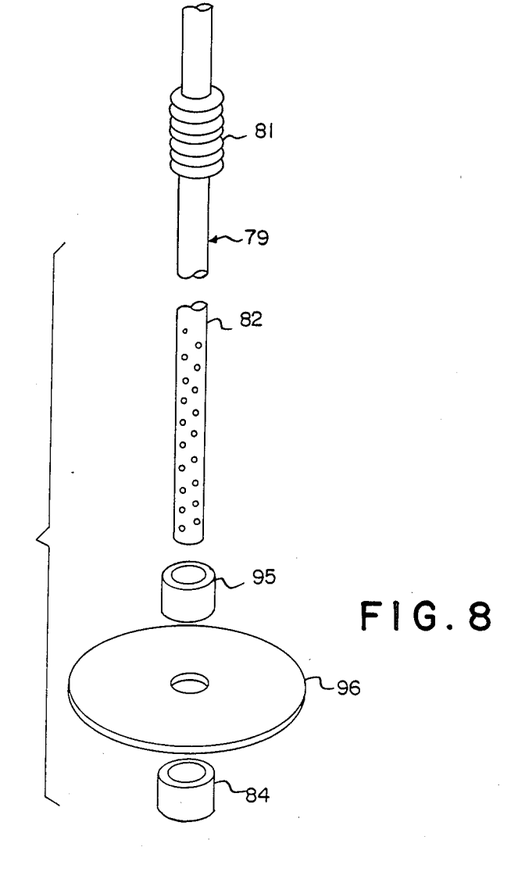
FIG. 8 is an exploded view of the alternate embodiment depicted in FIG. 7.

The alternate embodiment of the catheter system is assembled as shown in FIGS. 7 and 8. The fused end of the percutaneous neck 95 is placed onto the distal end of the catheter tube 82. The percutaneous neck 95 is then slid along the internal region of the catheter tube until the fused end of the percutaneous neck 95 is contiguous to the first convolution of the bellows 81. The percutaneous skirt 96 is then placed on the distal end of the catheter 82 and positioned just below the percutaneous neck 95. The neck 95 and skirt 96 are bonded to the catheter tube 79 with a solvent such as tetrahydrofuran (THF). The slidable peritoneal collar 84 is then positioned between the skirt/neck assembly and the punched holes at the distal end of internal portion 82 of the tube 79. Prior to implantation of the catheter system the peritoneal collar 84 is adjusted to fit the patient's peritoneum.

For implantation of the peritoneal catheter system either local or general anesthesia may be used. Preoperative antibiotics for wound prophylaxis are generally recommended, and sterile techniques are required.

For patients undergoing an initial catheter insertion selection of the left or right lower quadrant as the site for the skin button is recommended; however, the insertion position should not be on the belt-line or on a "skin fold". This site may be about one inch below and lateral to the Umbilicus. A template of the skin button is placed over the implant site and the circumference of the subdermal flange is outlined on the skin utilizing a skin marker. This identifies the margins of the subdermal dissection to be performed later. The outline of the percutaneous access device is then marked using the center hole of the template. The template is removed.

A circular coring knife is then positioned over the central marking, and a core of tissue approximately 7 mm deep is removed. This is accomplished by gently rotating the biopsy punch back and forth as it is advanced. A snug fit (not too loose or tight) around the neck region of the catheter is essential for optimal tissue ingrowth. Care must be taken to avoid excessive twisting and skewing of the coring knife so that the incision remains circular and adjacent tissue unharmed. The core of skin is removed and discarded.

Once the circular incision has been made, a number eleven scalpel blade is used to initiate dissection of a subdermal pocket for the skirt. This dissection is carried out in a radial fashion from the margin of the central core. The scalpel is only used to create a 2-3 mm incision sufficient to accommodate a pair of baby Metzenbaum scissors. It is important that baby Metzenbaum scissors be used since it is impossible to open standard Metzenbaum scissors sufficiently to carry out the dissection without distorting and traumatizing the central core. With the fingers of one hand on the skin over the implant site, a plane is created precisely at the subdermal-subcutaneous junction which is dissected to the margins of the marked skin. This dissection must be carried out with the utmost care to avoid removing too much of the vasculature while ensuring that no adispose tissue or debris is left at the tissue-biomaterial interface. Completion of this dissection will result in a subdermal pocket for the skirt.

The goal at this point is to create the incisions which are needed for inserting the catheter system into its final position. A transverse incision approximately 2 inches in length is made 2 inches inferior to the exit site and is carried down to the level of the peritoneum. The subcutaneous tissue at the lateral margin of the incision is then dissected off the underlying fascia in order to create a plane superficial to the skeletal muscle. This dissection is carried superiorly to an area directly beneath the circular incision. The floor of the superficial subdermal plane is incised transversely using the baby Metzenbaum scissors through the central core. Thus, the superficial subdermal plane communicates with the suprafascial plane beneath the subcutaneous tissue. This dissection is necessary to create a path for retrograde insertion of the system. Before doing this, a path must be created for the dialysis catheter itself from the subdermal plant to the peritoneum. This is accomplished by creating a subdermal tunnel from the subdermal pocket inferiorly for about 1.5-2 inches. This tunnel should end in the superior margin of the transverse incision at a level slightly below the subdermal plane to facilitate skin closure.

The catheter is then introduced in the following fashion. First, the internal end of the catheter is passed through the transverse incision, through the deep subcutaneous plane, up the subdermal pocket and through the tunnel back to the midline. The external catheter is then introduced through the transverse incision and the deep subcutaneous plane and out through the central core. The external catheter is now slowly pulled through the circular incision and the percutaneous access device eased up into its final seated position in the subdermal pocket. Absorbable sutures are used to close the incision below the flange to lock it firmly in place.

The distal end of the catheter 79, i.e. the internal portion 82 of the catheter below the flange, is passed through muscles (usually the oblique and transversalis muscles) to the peritoneum where a small incision is made exposing the intra-abdominal cavity. This incision should be smaller than the diameter of the catheter. The peritoneum is stretched over the catheter 79 as it is advanced inferiorly toward the pelvis. Placement of the distal end of lower portion 82 toward the center or left side of the abdomen is recommended. When the tip sits on the left side, the downward peristaltisis of the descending colon tends to keep the catheter directed toward the true pelvis. The internal catheter 82 should not be advanced against resistance. If significant resistance is encountered, the catheter 79 should be positioned laparoscopically. The peritoneal collar 84 may then be sewn to the external aspect of the peritoneum.

The final placement of the catheter may be seen in FIG. 2.

The catheter system must then be tested to confirm there is no obstruction to flow. To do so, a small volume of fluid (50 ml) may be infused in and out of the catheter. Once the catheter system is shown to be free of obstruction, the midline incision is closed in layers.

Once the wound has been closed, a non-stick dressing, such as the non-stick dressing sold under the trademark Telfa, should be applied around the catheter neck 24 and over the transverse incision. It is recommended that the non-stick dressing be cut lengthwise and a small notch cut in each half to fit around the catheter neck 24. The use of gauze is not recommended in that it can adhere to the porous percutaneous collar and traumatize the wound during its removal. For this reason, gauze dressing should be avoided. The catheter exits site and transverse incesion should be further protected by covering it with a transparent dressing. A suitable dressing is a Spandra® dressing, available from Thermedics Inc., of Woburn, Mass. The dressing may be applied directly over the wound site or may be precut to allow the catheter to exit through the bandage. The dressing may be left in place for up to five days.

It is to be understood that the forms of the peritoneal access catheter shown and described herein are preferred embodiments and that the device may be constructed of various other biocompatible materials and with some change in shape and size without departing from the spirit or scope of the invention. The invention is defined as all embodiments and their equivalents within the scope of the claims which follow.

What is claimed is:

1. A peritoneal access system comprising:
    a biocompatible percutaneous access device having a cylindrical neck portion for protrusion through the skin of a patient and an annular skirt portion for anchoring into the dermis/subcutaneous tissue interface said cylindrical neck portion having a textured surface to promote the ingrowth of the skin of the patient;
    a catheter tube threaded through said neck and skirt portions, said neck portion dividing said catheter tube into an external catheter region and an internal catheter region, said external catheter region comprising a flexible bellows which can form a 90 degree angle adjacent said neck and providing means for absorbing shock when the external catheter is moved and said internal region of said catheter being bent approximately 90 degrees, with relation to said neck portion, adjacent said skirt portion to direct the catheter away from the percutaneous access device; and
    a collar frictionally fit and slidably mounted directly on said internal region of said catheter so as to be adjustably positionable along the length of the internal region of said catheter during implantation into the peritoneum to be positioned in close approximation to the peritoneum regardless of the thickness of the patient's abdominal wall thickness.

2. A peritoneal access system comprising:
    a biocompatible percutaneous cylindrical neck for protrusion through the skin of a patient, said neck having a textured surface for encouraging ingrowth of skin of a patient;
    a biocompatible percutaneous annular skirt adjacent to said neck for anchoring into the dermis/subcutaneous tissue interface;

a catheter tube threaded through said neck and said skirt, said neck and said skirt serving to divide said catheter tube into an external catheter region and an internal catheter region;

said external catheter region comprising a flexible bellows capable of forming a 90 degree angle adjacent said neck an providing means for absorbing shock when said external region of said catheter tube is moved; and a collar frictionally fit and slidably mounted directly on said internal region of said catheter so as to be adjustably positionable along the length of the internal region of said catheter during implantation into the peritoneum to be positioned in close approximation to the peritoneum regardless of the thickness of the patient's abdominal wall thickness.

3. The peritoneal access system of claim 2 wherein said internal catheter region has a 90 degree angle adjacent said skirt to direct the catheter tube away from the percutaneous skirt.

4. The peritoneal access system of claim 2 wherein said neck and said skirt are bonded together.

5. The peritoneal access system of claim 2 wherein said neck and said skirt are independently mounted on said catheter tube.

6. The peritoneal access system of claim 2 wherein said collar and said neck are substantially identical.

7. The peritoneal access system of claim 2 wherein said neck has a textured surface for promotion of tissue ingrowth.

8. The peritoneal access system of claim 7 wherein said textured surface is formed of two or more layers of bias wrapped filament.

9. The peritoneal system of claim 7 wherein said skirt is formed of wrapped filaments fused together.

10. A method for accessing a patient's body comprising:

providing a biocompatible conduit capable of transferring a substance form a point external to the patient's body to within the patient's body, said conduit having a bellows to enable the bending of said conduit without trauma to the patient;

providing a means for anchoring said conduit to the patient's body, said anchoring means having a textured surface to promote ingrowth of tissue from the patient's body;

feeding said conduit through said anchoring means into the patient's body until said bellows is adjacent said anchoring means;

feeding said conduit through a frictionally fit collar within the patient's body said collar being capable of being adjustably positioned along the conduit;

bending a portion of said conduit which is inside of the patient's body and adjacent to said anchoring means approximately 90 degrees; and positioning the collar in close proximity to the patient's peritoneum.

11. A method for implanting a peritone comprising:

providing a percutaneous access device with a texture surface through which extends a catheter tube, said percutaneous access device when implanted serving to separate said catheter tube into external and internal portions, and said catheter tube including a bellows section on the external portion of the catheter tube, a sharp angle on the internal portion of the tube and a peritoneal collar slidably mounted on the internal portion of the catheter tube;

making incisions to remove a plug of skin tissue, to allow for insertion of the percutaneous access device at the subdermal-subcutaneous tissue interface, and to extend the catheter tube through the peritoneum;

determining the thickness of the abdominal wall and sliding the peritoneal collar along the internal portion of the catherter tube so that the internal end of the peritoneal collar will be positioned in close proximity to the outer surface of the peritoneum;

implanting the percutaneous access device at the subdermal-subcutaneous tissue interface;

positioning said peritoneal collar near the outer surface of the peritoneum;

bending the external portion of the catheter tube at the bellows section and taping at least part of the remaining external catheter tube to the patient's body.

12. A peritoneal access system comprising:

a biocompatible percutaneous cylindrical neck for protrusion through the skin of a patient, said neck having a textured surface formed of two or more layers of bias wrapped filament for encouraging ingrowth of skin of a patient;

a biocompatible percutaneous annular skirt adjacent to said neck for anchoring into the dermis/subcutaneous tissue interface;

a catheter tube threaded through said neck and said skirt, said neck and said skirt serving to divide said catheter tube into an external catheter region and an internal catheter region; and said external catheter region comprising a flexible bellows capable of forming a 90 degree angle adjacent said neck an providing means for absorbing shock when said external region of said catheter tube is moved.

13. A peritoneal access system comprising:

a biocompatible percutaneous cylindrical neck for protrusion through the skin of a patient, said neck having a textured surface for encouraging ingrowth of skin of a patient;

a biocompatible percutaneous annular skirt formed of wrapped filaments fused together said skirt being adjacent to said neck for anchoring into the dermis/subcutaneous tissue interface;

a catheter tube threaded through said neck and said skirt, said neck and said skirt serving to divide said catheter tube into an external catheter region and an internal catheter region; and said external catheter region comprising a flexible bellows capable of forming a 90 degree angle adjacent said neck an providing means for absorbing shock when said external region of said catheter tube is moved.

* * * * *